US007316930B1

(12) United States Patent
Montalbo

(10) Patent No.: US 7,316,930 B1
(45) Date of Patent: Jan. 8, 2008

(54) USE OF VERTICALLY STACKED PHOTODIODES IN A GENE CHIP SYSTEM

(75) Inventor: Joseph Domenick Montalbo, Menlo Park, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 666 days.

(21) Appl. No.: 10/421,647

(22) Filed: Apr. 21, 2003

(51) Int. Cl.
| | |
|---|---|
| G01N 21/76 | (2006.01) |
| G01N 1/10 | (2006.01) |
| G21K 5/00 | (2006.01) |
| H01L 21/00 | (2006.01) |
| C12Q 1/02 | (2006.01) |
| C12M 1/34 | (2006.01) |

(52) U.S. Cl. .................. 436/172; 250/458.1; 438/1; 435/29; 435/288.4; 356/246

(58) Field of Classification Search ................. 436/172; 250/458.1; 438/1; 435/29, 288.4; 356/246
See application file for complete search history.

(56) References Cited

U.S. PATENT DOCUMENTS

| | | | |
|---|---|---|---|
| 3,456,134 A | 7/1969 | Ko | |
| 4,177,800 A | 12/1979 | Enger | |
| 4,435,050 A | 3/1984 | Poler | |
| 4,508,766 A | 4/1985 | Inaike et al. | |
| 4,585,456 A | 4/1986 | Blackmore | |
| 4,928,172 A | 5/1990 | Uehara et al. | |
| 5,177,670 A | 1/1993 | Shinohara et al. | |
| 5,258,025 A | 11/1993 | Fedorov et al. | |
| 5,318,557 A | 6/1994 | Gross et al. | |
| 5,603,328 A | 2/1997 | Zucker et al. | |
| 5,604,531 A | 2/1997 | Iddan et al. | |
| 5,876,339 A | 3/1999 | Lemire | |
| 5,965,875 A * | 10/1999 | Merrill | ........................ 250/226 |

(Continued)

FOREIGN PATENT DOCUMENTS

JP          4-180736          6/1992

(Continued)

OTHER PUBLICATIONS

Lin, Gisela et al., May 20, 2004, "Improved Sensor Pills for Physiological Monitoring," pp. 1-2. Can be found at http://www.nasatech.com/Briefs/Feb00/NP020652.html.

(Continued)

*Primary Examiner*—Jill Warden
*Assistant Examiner*—Lore Ramillano
(74) *Attorney, Agent, or Firm*—Darby & Darby PC; John W. Branch

(57) ABSTRACT

An improved gene chip system is arranged with vertically stacked photodiodes for sensing luminescence of genetic material. When genetic samples are combined with a reagent in an array of wells on a substrate, the reaction may cause light of a specified color to emanate from certain well locations. Vertically stacked photodiodes are provided that sense each color and intensity of the light at each well location. The vertically stacked photodiodes provide an image sensor that may be integrally constructed with the substrate and wells used for a gene chip system. The illumination data, which includes which wells are luminescent, the color of light, and the intensity of light in each illuminated cell, may be analyzed to determine properties of the genetic sample.

12 Claims, 5 Drawing Sheets

U.S. PATENT DOCUMENTS

| | | | |
|---|---|---|---|
| 6,025,873 | A | 2/2000 | Nishioka et al. |
| 6,049,094 | A | 4/2000 | Penry |
| 6,057,909 | A | 5/2000 | Yahav et al. |
| 6,169,318 | B1 | 1/2001 | McGrath |
| 6,192,267 | B1 | 2/2001 | Scheminski et al. |
| 6,240,312 | B1 | 5/2001 | Alfano et al. |
| 6,261,226 | B1 | 7/2001 | McKenna et al. |
| 6,285,400 | B1 | 9/2001 | Hokari et al. |
| 6,300,612 | B1 | 10/2001 | Yu |
| 6,348,411 | B1 | 2/2002 | Ireland et al. |
| 6,425,858 | B1 | 7/2002 | Minami |
| 6,428,469 | B1 | 8/2002 | Iddan et al. |
| 6,607,301 | B1 | 8/2003 | Glukhovsky et al. |
| 6,632,175 | B1 | 10/2003 | Marshall |
| 6,638,304 | B2 | 10/2003 | Azar |
| 6,709,387 | B1 | 3/2004 | Glukhovsky et al. |
| 6,749,633 | B1 | 6/2004 | Lorenzo et al. |
| 6,764,440 | B2 | 7/2004 | Iddan et al. |
| 6,771,007 | B2 | 8/2004 | Tanielian |
| 6,828,908 | B2 | 12/2004 | Clark |
| 6,830,135 | B2 | 12/2004 | Lin et al. |
| 6,881,943 | B1 | 4/2005 | Yegnashankaran |
| 6,885,818 | B2 | 4/2005 | Goldstein |
| 6,895,270 | B2 | 5/2005 | Ostrovsky |
| 6,904,308 | B2 | 6/2005 | Frisch et al. |
| 7,041,493 | B2 * | 5/2006 | Rao .................. 435/288.1 |
| 7,044,908 | B1 | 5/2006 | Montalbo et al. |
| 2001/0035902 | A1 | 11/2001 | Iddan et al. |
| 2001/0051766 | A1 | 12/2001 | Gazdzinski |
| 2002/0032366 | A1 | 3/2002 | Iddan et al. |
| 2002/0042562 | A1 | 4/2002 | Meron et al. |
| 2002/0089595 | A1 | 7/2002 | Orava et al. |
| 2002/0103417 | A1 | 8/2002 | Gazdzinski |
| 2002/0103439 | A1 | 8/2002 | Zeng et al. |
| 2002/0107444 | A1 | 8/2002 | Adler |
| 2002/0109774 | A1 | 8/2002 | Meron et al. |
| 2002/0123325 | A1 | 9/2002 | Cooper |
| 2002/0173700 | A1 | 11/2002 | Kim et al. |
| 2002/0198470 | A1 | 12/2002 | Imran et al. |
| 2003/0020810 | A1 | 1/2003 | Takizawa et al. |
| 2003/0060683 | A1 | 3/2003 | Abe et al. |
| 2003/0117491 | A1 | 6/2003 | Avni et al. |
| 2003/0130562 | A1 | 7/2003 | Barbato et al. |
| 2003/0171653 | A1 | 9/2003 | Yokoi et al. |
| 2003/0195415 | A1 | 10/2003 | Iddan |
| 2003/0222223 | A1 * | 12/2003 | Kamei et al. ............ 250/458.1 |
| 2004/0027459 | A1 | 2/2004 | Segawa et al. |
| 2004/0032187 | A1 | 2/2004 | Penner et al. |
| 2004/0054278 | A1 | 3/2004 | Kimchy et al. |
| 2004/0073267 | A1 | 4/2004 | Holzer |
| 2004/0087832 | A1 | 5/2004 | Glukhovsky et al. |
| 2004/0092825 | A1 | 5/2004 | Madar et al. |
| 2004/0106849 | A1 | 6/2004 | Cho et al. |
| 2004/0111011 | A1 | 6/2004 | Uchiyama et al. |
| 2004/0249245 | A1 | 12/2004 | Irion |
| 2004/0254455 | A1 | 12/2004 | Iddan |

FOREIGN PATENT DOCUMENTS

| | | |
|---|---|---|
| WO | WO-94/23334 | 10/1994 |
| WO | WO-01-53792 | 7/2001 |

OTHER PUBLICATIONS

Lin, Gisela and William Tang, May 20, 2004, "Wearable Sensor Patches for Physiological Monitoring," pp. 1-2. Can be found at http://www.nasatech.com/Briefs/Feb00/NP020651.html.

Astares, Alexander et al., Dec. 4-7, 2002, "A miniature Integrated Electronics Sensor Capsule for Real-Time Monitoring of the Gastrointestinal Tract (IDEAS)." ICBME 2002: "The Bio-Era: New Challenges, New Frontiers." pp. 1-2.

* cited by examiner

USE OF VERTICALLY STACKED PHOTODIODES IN A GENE CHIP SYSTEM

FIELD OF THE INVENTION

The present invention relates generally to photodiode technology. More particularly, the present invention relates to a gene chip system using vertically stacked photodiodes.

BACKGROUND OF THE INVENTION

Imaging sensors are commonly used in various applications such as digital cameras. The imaging sensor includes multiple pixel sensors that are arranged in an array. Light is reflected from a scheme and received by the imaging sensor. The imaging sensor provides signal outputs that have magnitudes that correspond to the light intensity level for each pixel sensor within the array.

Conventional color imaging sensors use a color filter mosaic to select different wavelength bands at different photodiode locations. The photodiodes for these color filter mosaics are arranged to detect as wide a range of the color spectrum as possible while using color filters to limit the detection to a single desired color. One example of a color filter mosaic is the Bayer color filter array as shown in FIG. 1. The Bayer color filter array (100) has green pixels (G) arranged in a checkerboard and alternating lines of red (R) and blue (B) pixels to fill in the remainder of the pattern. The Bayer color filter array takes advantage of the human eye's sensitivity to high spatial frequencies in luminance, which is primarily composed of green light. The Bayer color filter array therefore improves the perceived sharpness of the digital image.

A gene chip system as shown in FIG. 2 is often used in conjunction with an image sensor using a Bayer color filter array. The gene chip system (200) includes a substrate (212) with multiple wells (e.g., 211) in which a reagent (e.g., 216) is deposited. The reagent has a specified DNA signature. Also, an amount of genetic material or genetic sample (e.g., 214) is deposited into each of the wells (e.g., 211). Depending on the reagent and genetic sample used, a match or mismatch will occur within the well, and the material within the well may fluoresce at a specified color. Accordingly, the array of wells (e.g., 211) on the substrate (212) includes wells of different colors and color intensities of fluorescent light or other luminescence after the genetic sample is deposited. The image sensor (202) senses the light from the luminescent wells to provided data regarding the relative position, color, and intensity of the light within the array of the gene chip system. A Bayer color filter array or other color filter mosaic may be used with the image sensor (202) in capturing the image provided by the luminescent genetic samples (e.g., 214). The image sensor is positioned away from the array of wells to capture an image of the entire array. The image illustrates which of the wells are emanating light and the color of the light. Which wells are luminescent and the color of the light provides information regarding properties of the genetic sample used.

SUMMARY OF THE INVENTION

An improved gene chip system is provided that is arranged with vertically stacked photodiodes for sensing luminescence of genetic material. When genetic samples are combined with a reagent in an array of wells on a substrate, the reaction may cause light of a specified color to emanate from certain well locations. Vertically stacked photodiodes are provided that sense each color and intensity of the light (e.g., as in U.S. Pat. No. 5,965,875) at each well location. The vertically stacked photodiodes provide an image sensor that may be integrally constructed with the substrate and wells used for a gene chip system. The illumination data, which includes which wells are luminescent, the color of light, and the intensity of light in each illuminated cell, may be analyzed to determine properties of the genetic sample.

In one aspect of the present invention, a gene chip system is provided that comprises a substrate that includes an array of wells. Each of the wells are arranged to receive an amount of a genetic sample. Vertically stacked photodiodes correspond to each of the wells in the array of wells. Each vertically stacked photodiode is arranged to sense light emanating from its corresponding well such that illumination data is received for the array of wells. The illumination data provides analysis of properties related to the genetic sample. The vertically stacked photodiodes may be integrally constructed with the substrate. The vertically stacked photodiodes may also be positioned opposite the substrate from the array of wells included in the substrate. Accordingly, the light emanating from illuminated wells within the array of wells is transmitted across the substrate to reach the vertically stacked photodiodes. Transmitting the light across the substrate results in a distance for light to travel between one of the wells of the array and its corresponding vertically stacked photodiodes that is less than a thickness associated with the substrate.

In another aspect of the present invention, a method is provided for analyzing a genetic sample in a gene chip system. The method comprises combining the genetic sample with a reagent in an array of well locations on a substrate, and sensing each color of light that is emanating from each of the well locations. The light is sensed according to the absorption level of light into vertically stacked photodiodes corresponding to each of the well locations. Illumination data is received for each of the well locations that correspond to each color of light that is sensed for those well locations. The illumination data may then be analyzed to determine properties related to the genetic sample. A digital image may also be produced that corresponds to the illumination data. The digital image illustrates which of the well locations is illuminated and the color and intensity of each illuminated well location.

In still a further aspect of the present invention, a gene chip system is provided that comprises means for combining a genetic sample with a reagent in an array of well locations on a substrate, means for sensing each color of light that is emanating from each of the well locations, means for receiving illumination data for each of the well locations that corresponds to each color of light that is sensed for those well locations, and means for analyzing the illumination data to determine properties related to the genetic sample.

A more complete appreciation of the present invention and its improvements can be obtained by reference to the accompanying drawings, which are briefly summarized below, the following detail description of presently preferred embodiments of the invention, and the appended claims.

DETAILED DESCRIPTION OF THE PREFERRED EMBODIMENT

The present invention provides a gene chip system that uses vertically stacked photodiodes to detect luminescence within an array of sample locations resulting from a reaction between a genetic sample and a reagent. The present invention provides an integrated gene chip system where the image sensors may be integrated with the substrate that receives the genetic sample and the reagent. Previously, the image sensor was often required to be separated from the substrate for previous applications where a color filter mosaic (e.g., the Bayer pattern) was used. The separation ensured that the reagent would not react with the color filters over the pixels within the image sensor. The color filters may be made from polymers or materials that may react with the reagent, affecting the chemical reactions occurring on the substrate containing the genetic sample. In the present application, color filters are not required since each color of light is sensed at each pixel location by the vertically stacked photodiodes. Accordingly, the image sensor of vertically stacked photodiodes may be integrally constructed with the substrate for holding the genetic sample, reducing the size of the gene chip system and improving tolerance levels.

Figure 3:
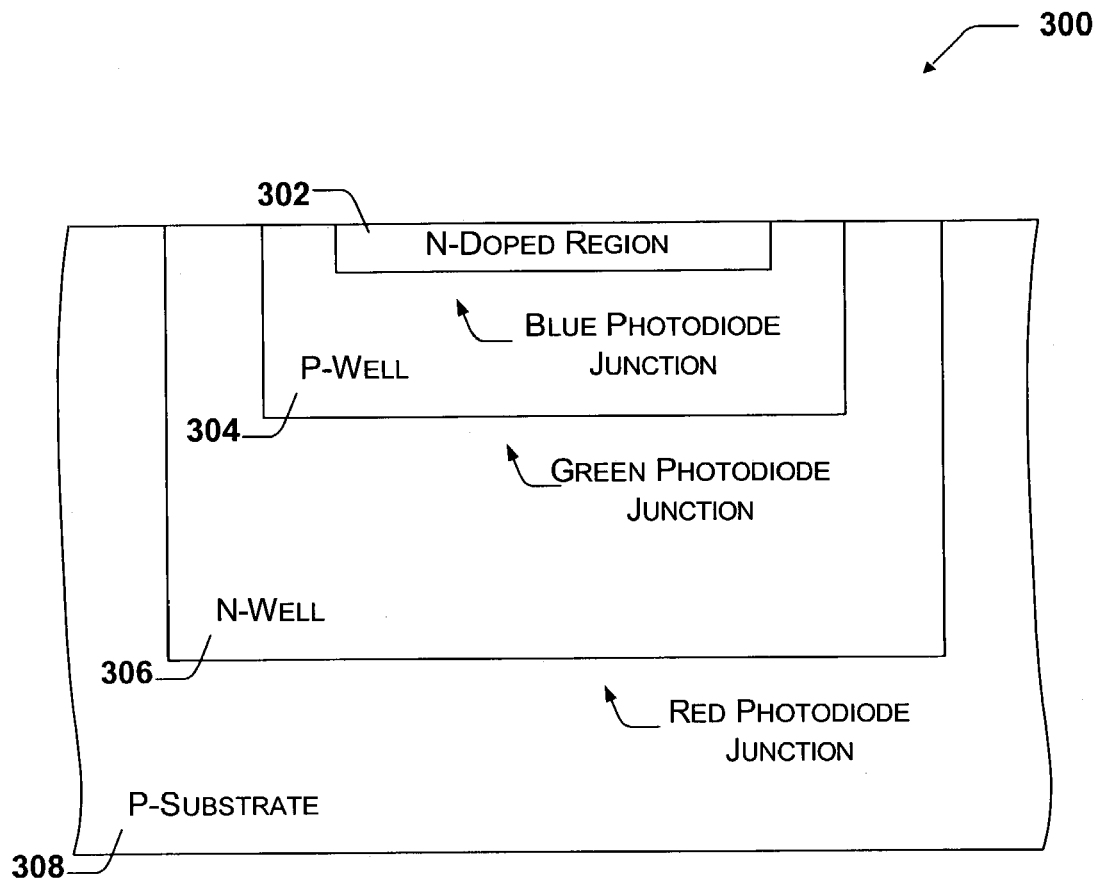
FIG. 3 is a partial cross-sectional view of a triple-well or vertically stacked photodiode cell.

FIG. 3 illustrates a partial cross-sectional view of a vertically stacked photodiode cell for use with the present invention. The vertically stacked photodiode cell (300) takes advantage of the differences in absorption length in silicon of light. Light of different wavelengths is absorbed in silicon at different lengths. The vertically stacked photodiode cell places blue, green, and red collection layers at different depths within the cell to measure different colors in the same pixel location.

Described differently, when light is absorbed in the active area of silicon, an electron-hole pair is formed. The electrons and holes are separated, with electrons passing to the "n" region and holes to the "p" region. The movement of electrons and holes to their respective regions generates a current in response to the light, allowing the light to be measured. The depth at which the electron-hole pair is formed is proportional to energy of the light that is proportional to the color of the light. Blue light, having the shortest wavelength, is absorbed near the top of a silicon cell. Green light, having a longer wavelength, is absorbed deeper in a silicon cell than blue light. Red light has a longer wavelength than both blue and green light and is absorbed deeper in a silicon cell than both blue and green light. A measurement for each color is received by measuring the current generated at different collection layers within the vertically stacked photodiode cell (300). The vertically stacked photodiode cell is arranged with pn junctions at selected depths within the silicon to form photodiodes. The pn junction between the n-doped region (302) and the p-well (304) forms a blue-sensitive photodiode, the pn junction between the p-well (304) and the n-well (306) forms a green sensitive photodiode, and the pn junction between the n-well (306) and the p-substrate (308) forms a red sensitive photodiode. This vertically stacked photodiode cell architecture allows the colors of light (blue, green, red) to be measured at a single pixel location. Vertically stacked photodiode cell architectures other than the exemplary architecture shown may also be used with the present invention without departing from the scope of the invention.

Figure 1:
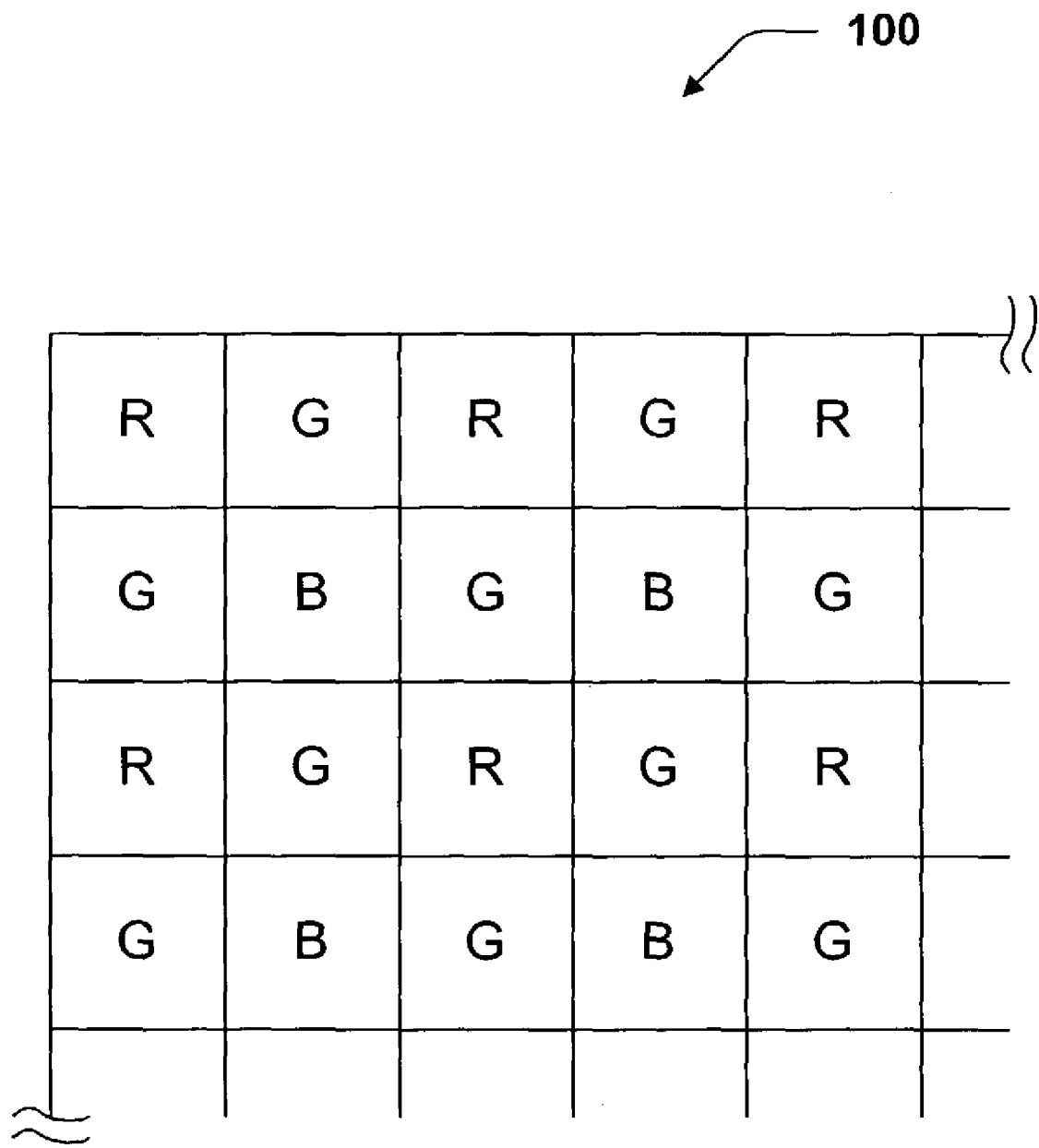
FIG. 1 illustrates the Bayer color filter array pattern.
Figure 2:
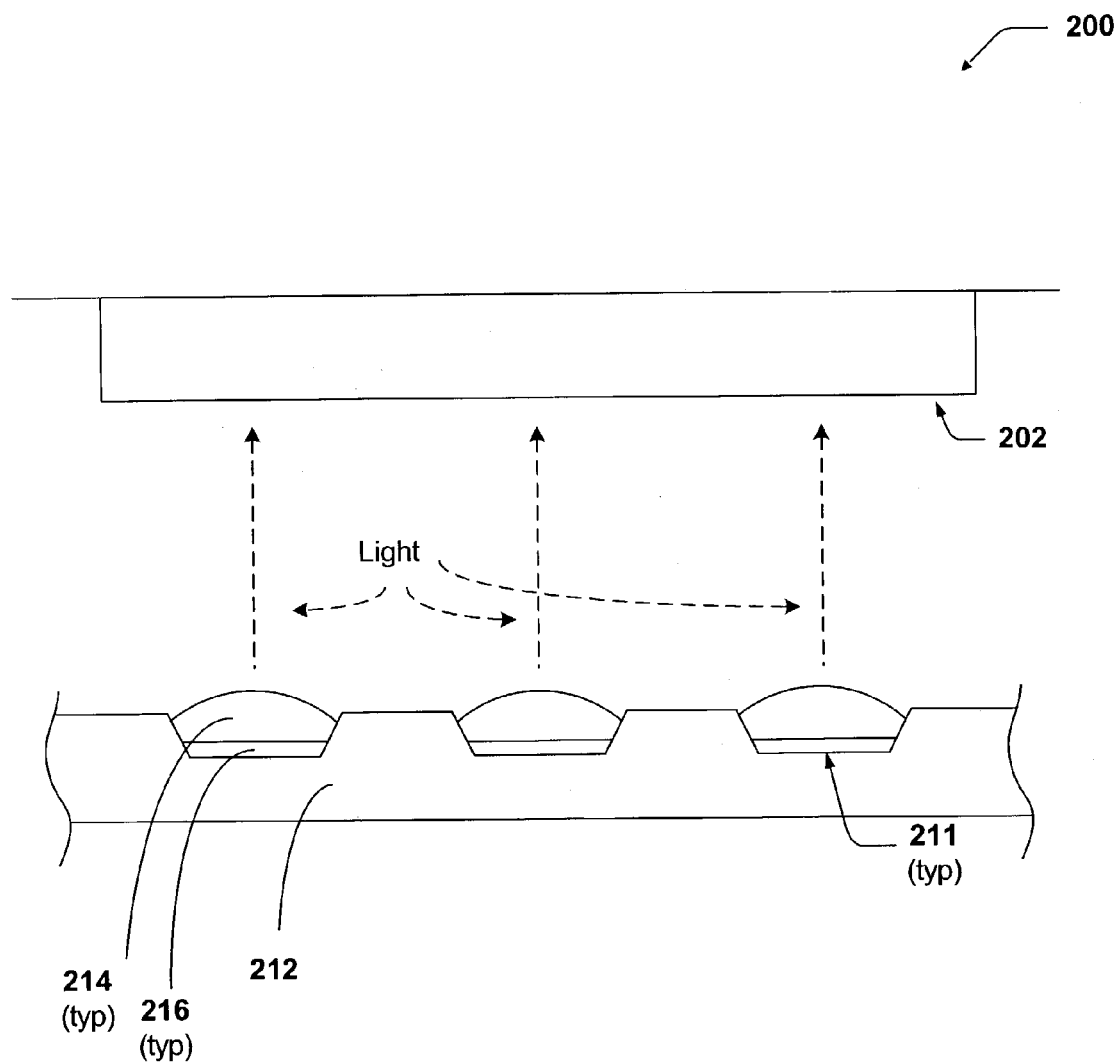
FIG. 2 is a partial cross-sectional view of an exemplary gene chip system using a conventional image sensor.
Figure 4:
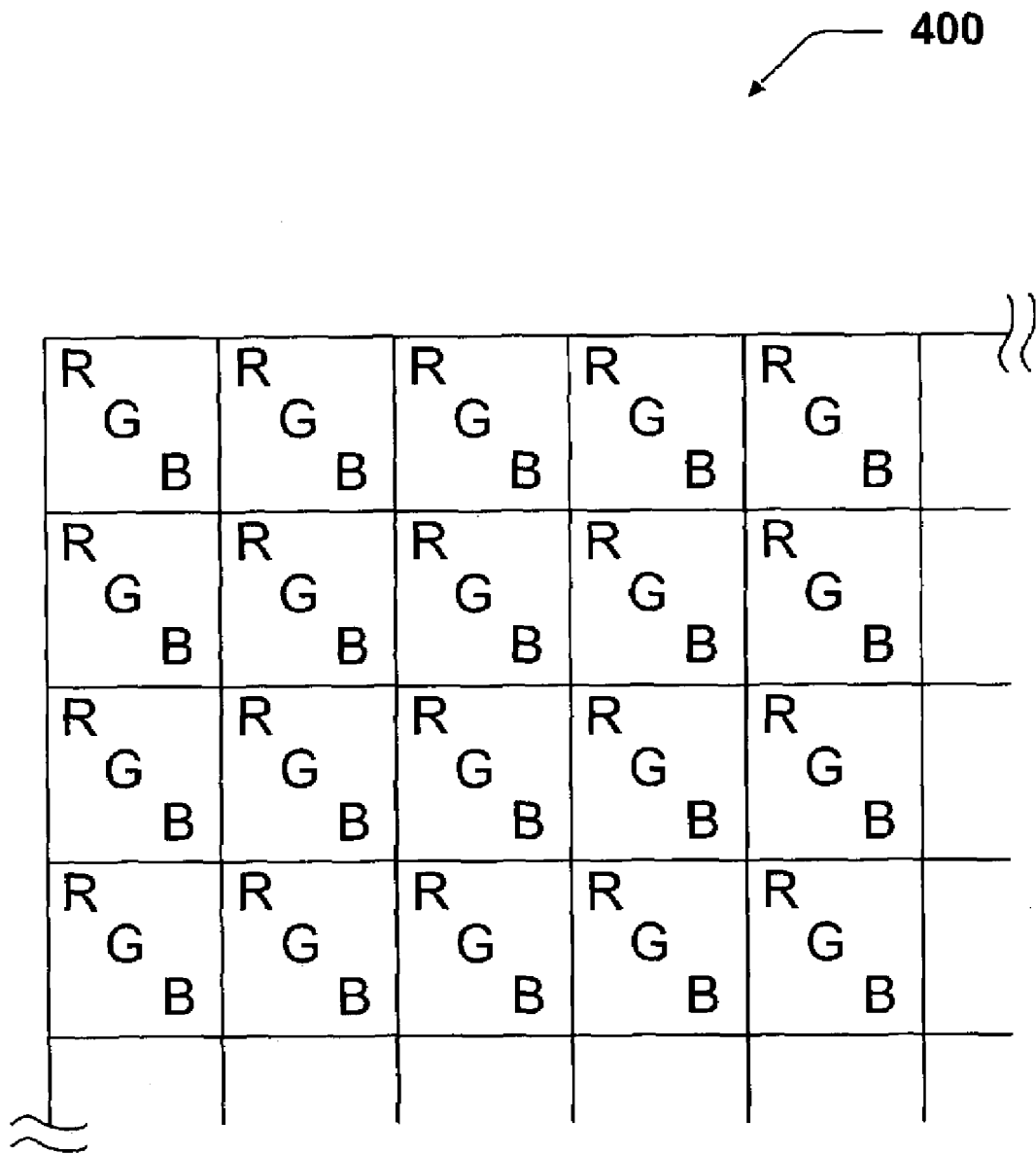
FIG. 4 is an exemplary color array pattern that corresponds to a vertically stacked pixel array.

FIG. 4 is an exemplary color array pattern that corresponds to a vertically stacked photodiode array. The color array pattern illustrates that each pixel location senses all three colors (blue, green, red) corresponding to the use of vertically stacked photodiodes. The illustration of the color pattern for a vertically stacked photodiode array is provided in contrast to the Bayer filter array pattern shown in FIG. 1.

Figure 5:
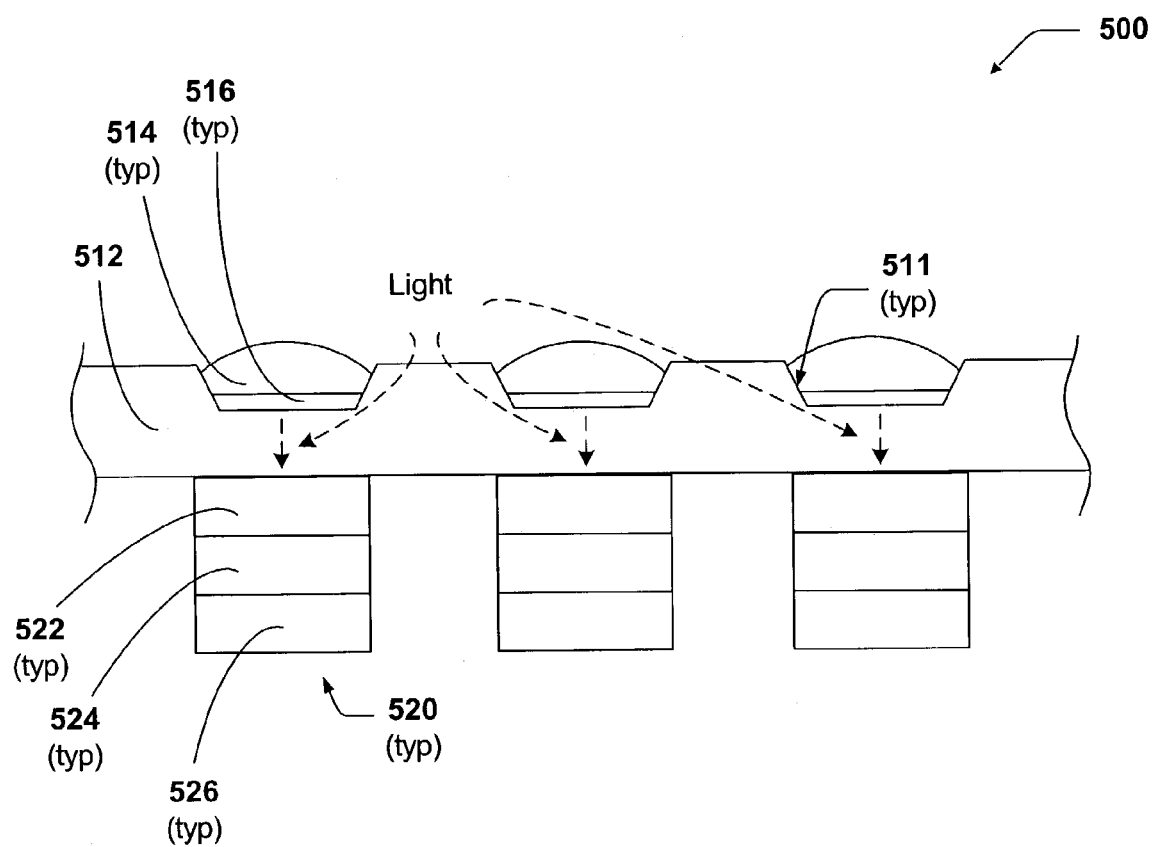
FIG. 5 is a partial cross-sectional view of vertically stacked photodiodes used in a gene chip system, in accordance with the present invention.

FIG. 5 is a partial cross-sectional view of vertically stacked photodiodes used in a gene chip system. The gene chip system (500) includes a substrate (512) and vertically stacked photodiodes (e.g., 520).

The substrate includes an array of wells (e.g., 511). Each well is arranged to receive an amount of a selected genetic material (e.g., 514) and a selected reagent (e.g., 516). The wells may be arranged as a microarrays with a well size that accepts a sample of 0-200 microns, or as a macroarray where samples may be 200 microns or more. The substrate (512) may be of any shape or size. In one embodiment, the substrate (512) is manufactured from glass, silicon, nylon substrates, or other materials that are non-reactant to the genetic sample or the reagent. In one embodiment, the substrate (512) is transparent such that light emanating from a well (e.g., 511) in the substrate is transmitted through the substrate.

Vertically stacked photodiodes (e.g., 520) are positioned in relation to each well (e.g., 511) of the substrate (512) to sense the light emanating from the well. In one embodiment, vertically stacked photodiodes are positioned opposite the substrate (512) from the well as shown in FIG. 5. In this embodiment, the light from the well (e.g., 511) is transmitted through the substrate (512) to reach the vertically stacked photodiodes. In an alternative embodiment, vertically stacked photodiodes may be positioned above each well with an alternative method (e.g., an injection method) for depositing the genetic sample and reagent within each well. The vertically stacked photodiodes may also be constructed similar to the vertically stacked photodiode cell described in FIG. 3.

When the genetic sample (e.g., 514) and the reagent (e.g., 516) are combined in a well, the reaction may result in illumination of the well. The vertically stacked photodiodes corresponding to the well sense the light with each color of illumination sensed at the single well location. In previous applications, the image sensor was required to be spatially separated from the well in order to sense each color from the well. In the present invention, distance of the image sensor from the well is minimized by using vertically stacked photodiodes at each well location to sense each of the colors of light (e.g., blue, green, red). As previously stated, the color sensed by each photodiode makes use of the absorption level of wavelengths of light in silicon. Accordingly, in one embodiment, vertically stacked photodiodes are stacked with a blue-sensitive photodiode (e.g., 522) closest to the well, a green-sensitive photodiode (e.g., 524) further from the well than the blue-sensitive photodiode, and a red-sensitive photodiode (e.g., 526) furthest from the well. As previously stated, sensing each of the colors at each well location allows for elimination of the use of color filters. Accordingly, the color filters do not interfere with the reaction between the genetic sample and the reagent. Also, the vertically stacked photodiodes (e.g., 520) and the substrate (512) containing the array of wells may be integrally constructed, reducing the size and complexity of the gene chip system (500).

The above specification, examples and data provide a complete description of the manufacture and use of the composition of the invention. Since many embodiments of the invention can be made without departing from the spirit and scope of the invention, the invention resides in the claims hereinafter appended.

I claim:

1. A gene chip system, comprising:
a substrate that includes an array of wells, wherein each of the wells receives and holds an amount of genetic sample and reagent; and vertically stacked photodiodes, wherein each of the vertically stacked photodiodes are integrally constructed with the substrate and are located adjacent to and fixed below each one of the wells in the array of wells, and wherein each vertically stacked photodiodes senses light emanating from its corresponding well.

2. The gene chip system as in claim 1, wherein the substrate is one of a group comprising glass, nylon, and silicon.

3. The gene chip system as in claim 1, wherein each vertically stacked photodiode is sensitive to a particular color of light emanating from its respective well, and wherein particular colors include, but are not limited to, blue, green and red.

4. The gene chip system as in claim 1, wherein the vertically stacked photodiodes located adjacent to and corresponding to one of the array of wells comprise a blue-sensitive photodiode, a green-sensitive photodiode, and a red-sensitive photodiode.

5. The gene chip system as in claim 4, wherein the blue-sensitive diode is closest to the one of the array of wells when compared to the green-sensitive photodiode and a red-sensitive photodiode, the green-sensitive photodiode is further from the one of the array of wells when compared to the blue-sensitive photodiode and closer to the one of the array of wells when compared to the red-sensitive photodiode, and the red-sensitive photodiode is furthest from the one of the array of wells when compared to the green-sensitive photodiode and a blue-sensitive photodiode.

6. The gene chip system as in claim 1, wherein the substrate is a transparent material.

7. The gene chip system as in claim 6, wherein the vertically stacked photodiodes are positioned opposite the substrate from the array of wells included in the substrate, such that light emanating from illuminated wells within the array of wells is transmitted across the substrate to reach the vertically stacked photodiodes.

8. The gene chip system as in claim 1, wherein
the substrate has a first surface and a second surface opposite the first surface and separated therefrom by a thickness associated with the substrate,
each well is formed as a depressed region in the first surface having a thickness that is less than the thickness associated with the substrate in another region, and
the distance for light to travel between one of the array of wells and its corresponding vertically stacked photodiodes is less than the thickness associated with the substrate.

9. The gene chip system as in claim 1, wherein the vertically stacked photodiodes receive illumination data corresponding to a color and an intensity of light; and wherein the gene chip system further comprises:
an analyzer for analyzing illumination data to determine properties related to the genetic sample.

10. The gene chip system as in claim 9, wherein the analyzer is arranged to output a digital image that illustrates the color and the intensity of light emanating from each illuminated well.

11. The gene chip system as in claim 1, wherein the vertically stacked photodiodes are integrally constructed in the substrate arranged for combining the genetic sample with a reagent.

12. The gene chip system as in claim 1, wherein the vertically stacked photodiodes are positioned on an opposite side of the substrate that is arranged to combine a genetic sample with a reagent from the array of wells, such that light emanating from an illuminated well is transmitted across this arrangement of the substrate to at least one of the vertically stacked photodiodes.

* * * * *

UNITED STATES PATENT AND TRADEMARK OFFICE
CERTIFICATE OF CORRECTION

PATENT NO. : 7,316,930 B1 Page 1 of 1
APPLICATION NO. : 10/421647
DATED : January 8, 2008
INVENTOR(S) : Montalbo It is certified that error appears in the above-identified patent and that said Letters Patent is hereby corrected as shown below:

In column 5, line 10, in Claim 1, before "genetic" insert -- a --.

In column 5, line 16, in Claim 1, delete "photodiodes" and insert -- photodiode --, therefor.

Signed and Sealed this

Twentieth Day of May, 2008

JON W. DUDAS
*Director of the United States Patent and Trademark Office*